United States Patent
Thurston, III

(10) Patent No.: US 7,973,977 B2
(45) Date of Patent: Jul. 5, 2011

(54) SYSTEM AND METHOD FOR REMOVING SEMI-TRANSPARENT ARTIFACTS FROM DIGITAL IMAGES CAUSED BY CONTAMINANTS IN THE CAMERA'S OPTICAL PATH

(75) Inventor: Kimball Darr Thurston, III, Los Angeles, CA (US)

(73) Assignee: Reliance Media Works, Burbank, CA (US)

( * ) Notice: Subject to any disclaimer, the term of this patent is extended or adjusted under 35 U.S.C. 154(b) by 791 days.

(21) Appl. No.: 11/804,605

(22) Filed: May 18, 2007

(65) Prior Publication Data

US 2007/0274606 A1    Nov. 29, 2007

(51) Int. Cl.
*H04N 1/407* (2006.01)
*H04N 1/409* (2006.01)

(52) U.S. Cl. ........ 358/3.26; 358/1.9; 358/436; 358/531; 345/611; 348/241; 348/245; 348/246; 348/252; 348/247; 348/335; 382/260; 382/261; 382/262; 382/263; 382/264; 382/265; 382/266; 382/275; 382/206; 382/228; 382/254

(58) Field of Classification Search ........................ None
See application file for complete search history.

(56) References Cited

U.S. PATENT DOCUMENTS

| | | | | |
|---|---|---|---|---|
| 4,356,398 A * | 10/1982 | Komaki et al. | ............... | 250/582 |
| 6,253,022 B1 * | 6/2001 | Strolle et al. | ................... | 386/109 |
| 2003/0210045 A1 * | 11/2003 | Mitchell et al. | ............... | 324/307 |
| 2004/0042682 A1 * | 3/2004 | Jia et al. | ........................ | 382/275 |
| 2004/0213480 A1 * | 10/2004 | Morton | ......................... | 382/269 |
| 2005/0068446 A1 * | 3/2005 | Steinberg et al. | ............. | 348/335 |

* cited by examiner

*Primary Examiner* — Twyler L Haskins
*Assistant Examiner* — Miya J Cato
(74) *Attorney, Agent, or Firm* — Benman, Brown & Williams

(57) ABSTRACT

A method and system for retouching digital images for a motion picture removes semi-transparent artifacts or 'blotches' caused by contaminates in the optical path of the camera. This approach provides the benefit of only having to retouch a single average image that is than automatically applied via a correction power map to the entire sequence of images for the affected scene. The formation of an average image tends to reinforce the artifacts making them easier to identify and reduce background detail making it easier to retouch the artifact.

26 Claims, 10 Drawing Sheets

FRAME 1

FRAME 2

FRAME N

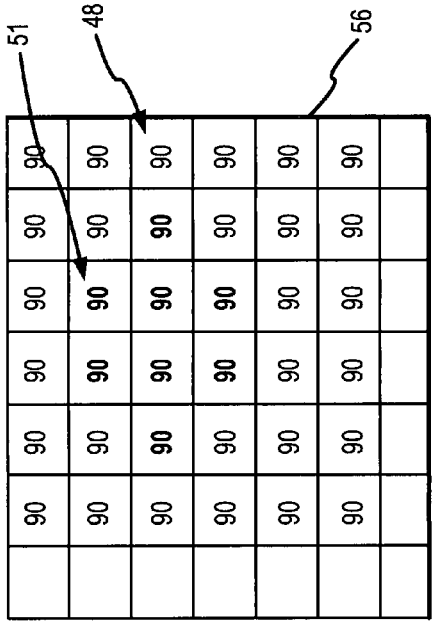
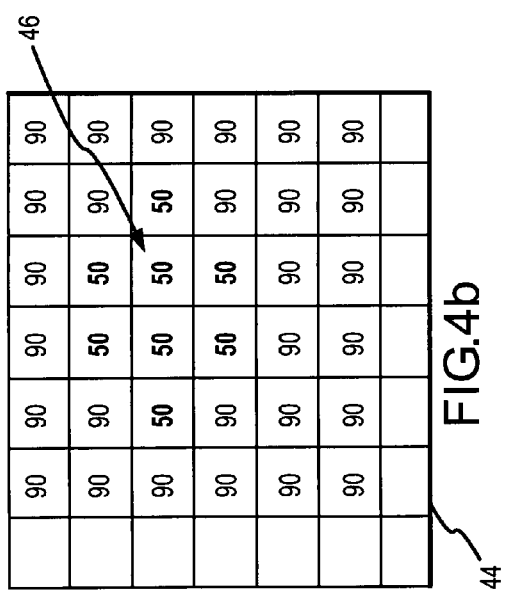
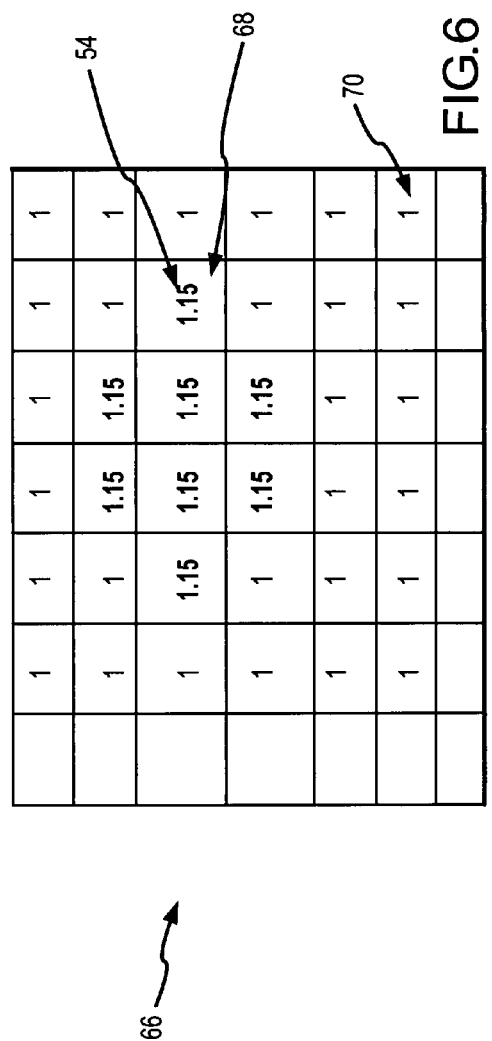

FRAME 1

FRAME 2

FRAME N

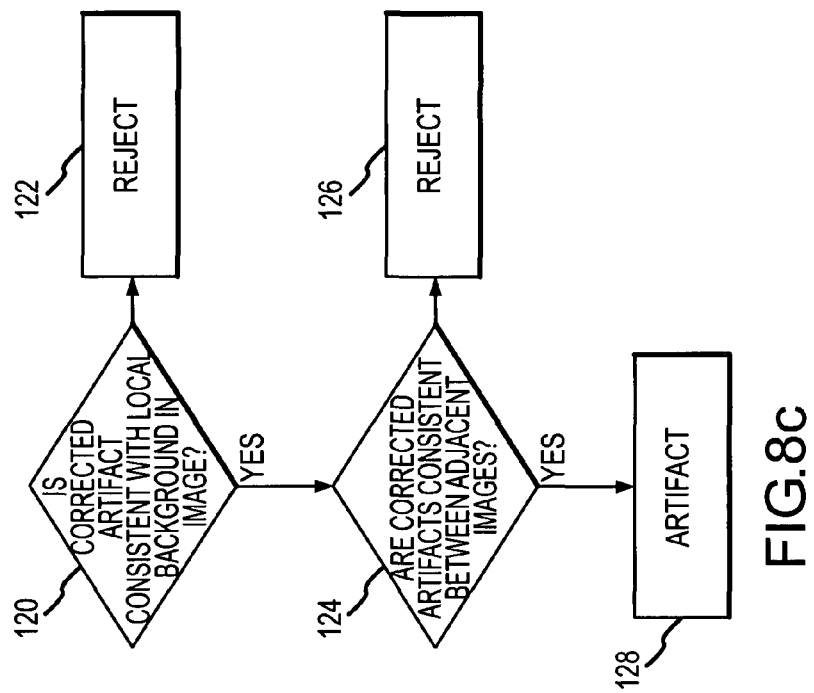
FIG.8c
FIG.8b
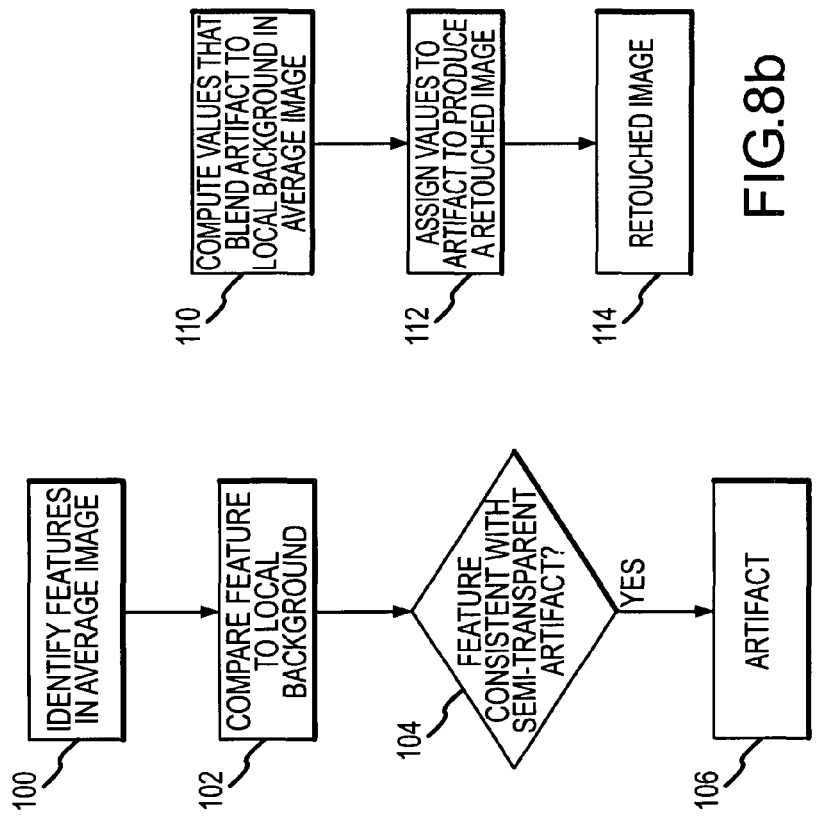
FIG.8a

SYSTEM AND METHOD FOR REMOVING SEMI-TRANSPARENT ARTIFACTS FROM DIGITAL IMAGES CAUSED BY CONTAMINANTS IN THE CAMERA'S OPTICAL PATH

BACKGROUND OF THE INVENTION

1. Field of the Invention

This invention relates to semi-transparent artifacts or 'blotches' that are introduced onto film or a digital image by contaminants in the camera's optical path, and more particular to an efficient method of removing these blotches.

2. Description of the Related Art

Digital and film cameras have a series of lenses 10 that capture light 12 from a scene for a motion picture and project it onto a image plane 13 where it is captured by a recording mechanism 14 such as a digital sensor or film. When the lenses 10 or other elements in the optical path such as dust cover 16 are not properly cleaned, contaminants 18 such as small water spots, thumb prints or small pieces of dirt can accumulate inside the lenses or close to the focal plane 20 of the camera. The miniscule contaminant, shown here on dust cover 16, is projected onto a much larger area in the image plane 13 where it forms an artifact 22 that is captured by the digital sensor or on the film. These blotches are very noticeable when watching a sequence of images.

If the problem is discovered during shooting, the lenses can be cleaned and the scenes reshot. However, the more typical situation is that the problem is not discovered until post-production. At this point, there are three options to handle artifacts. The first option is to do nothing and live with the artifacts, which given the production standards of $1^{st}$ run feature films and the transition to digital cinema is an unattractive option. The second option is to reshoot the affected scenes, which can be cost and time prohibitive. The third option is to manually retouch the affected digital images in post-production. Because the content of the imagery is generally changing throughout the scene, to ensure quality each and every image is typically individually retouched. This can take considerable tedious manual labor as the number of contaminated images in a scene can number into the several thousand.

SUMMARY OF THE INVENTION

The present invention provides an efficient method and system for retouching digital images for a motion picture to remove semi-transparent artifacts or 'blotches' caused by contaminates in the optical path of the camera. This approach provides the benefit of only having to retouch a single average image that is than automatically applied via a correction power map to the entire sequence of images for the affected scene. The formation of an average image tends to reinforce the artifacts making them easier to identify and reduce background detail making it easier to retouch the artifact.

This is accomplished by accumulating a plurality of contaminated digital images to produce an average image that isolates spatially fixed, temporally persistent features in a background that converges to a temporal low frequency measure of the images. The semi-transparent artifacts are downselected from the isolated features and retouched to resemble the background around the artifact. Downselection and retouching can be done manually using the computer software tool or with an automated software application. A correction power for each pixel in each artifact (in each color component) is computed as a non-linear coefficient between the average image and the retouched image. The correction powers for a given pixel may be determined from only amplitude information in the average and retouched images for that given pixel or it may be a statistical measure from amplitude information for multiple pixels in the artifact. Each contaminated image is corrected by raising each artifact pixel to its correction power to produce a retouched image. For simplicity, a map of correction powers may be determined and then applied to the entire contaminated image in which non-artifact pixels are assigned a value of one. A smoothing filter may be applied to the retouched areas. The retouched areas may be validated by a person viewing the sequence at normal speed or by a computer prior to release to further ensure quality.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 4a and 4b are a pictorial diagram of the accumulated average image and a numeric diagram of a color plane of the average image;

FIGS. 5a and 5b are a pictorial diagram of the retouched average image and a numeric diagram of a color plane of the retouched image;

FIG. 6 is the correction map for a color plane;

FIGS. 8a-8c are flowcharts of embodiments to automate the downselection, retouching and validation steps.

DETAILED DESCRIPTION OF THE INVENTION

Figure 1:
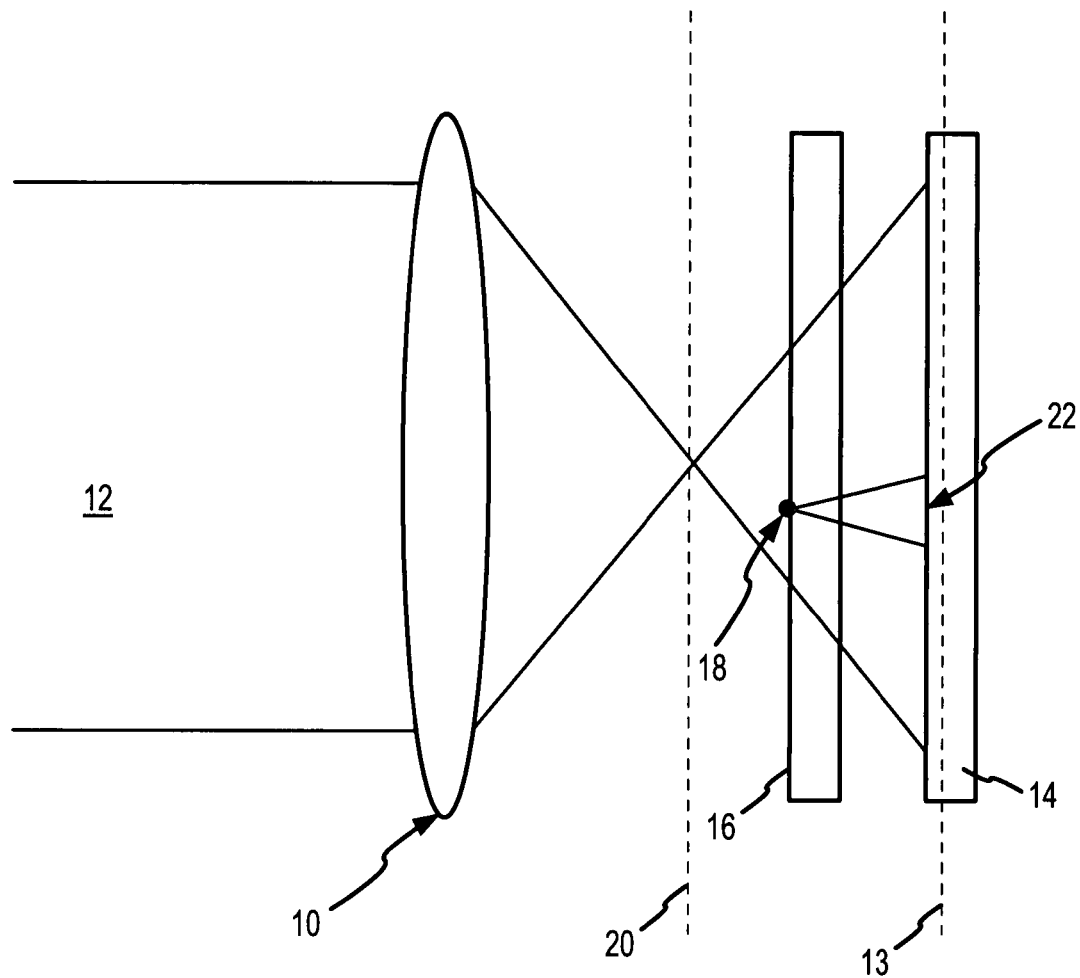
FIG. 1, as described above, is a diagram of a camera's optical system with a contaminant in the focal path that projects onto the sensor to form an artifact on the captured digital image.
Figure 2A:
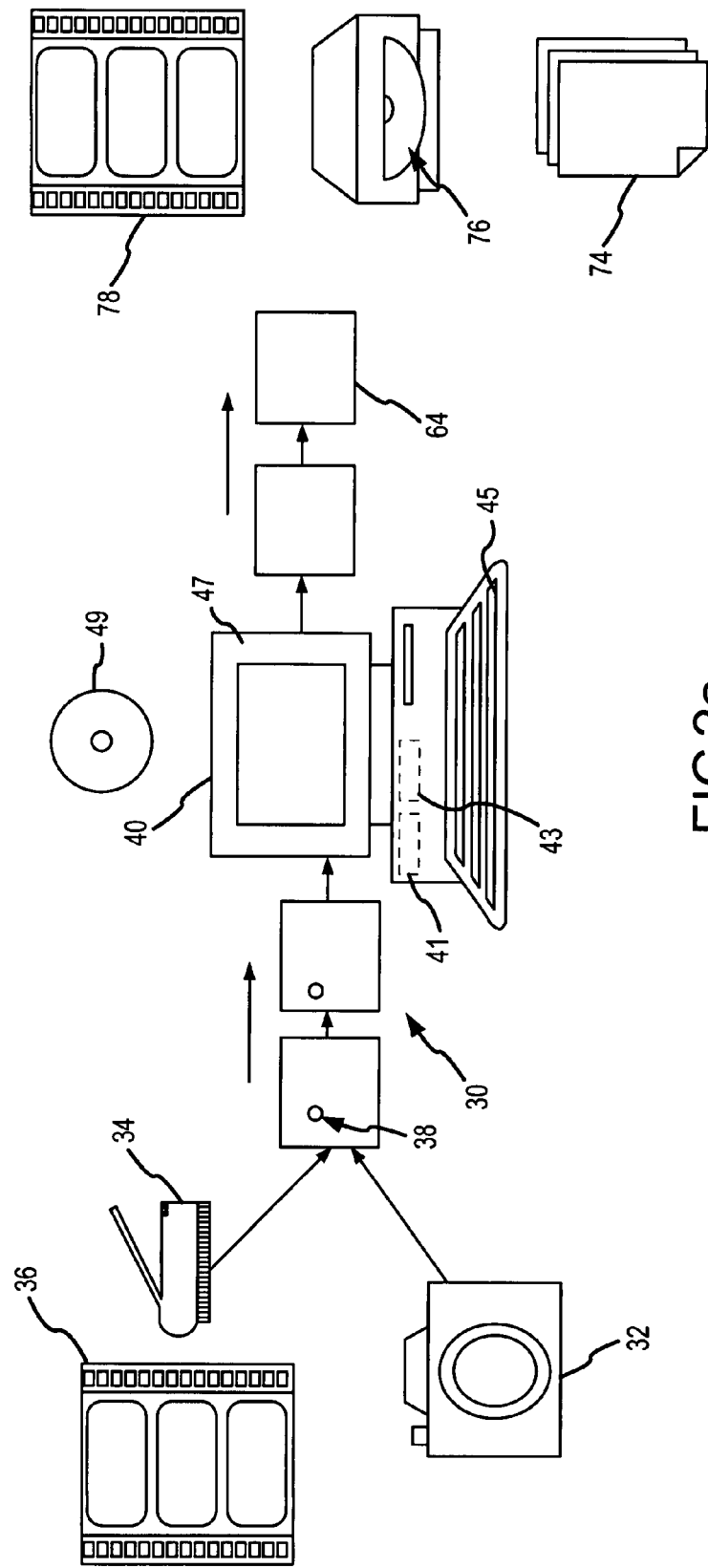
FIGS. 2a and 2b are a workstation and a flowchart of a method for removing semi-transparent artifacts from digital images in accordance with the present invention.
Figure 2B:
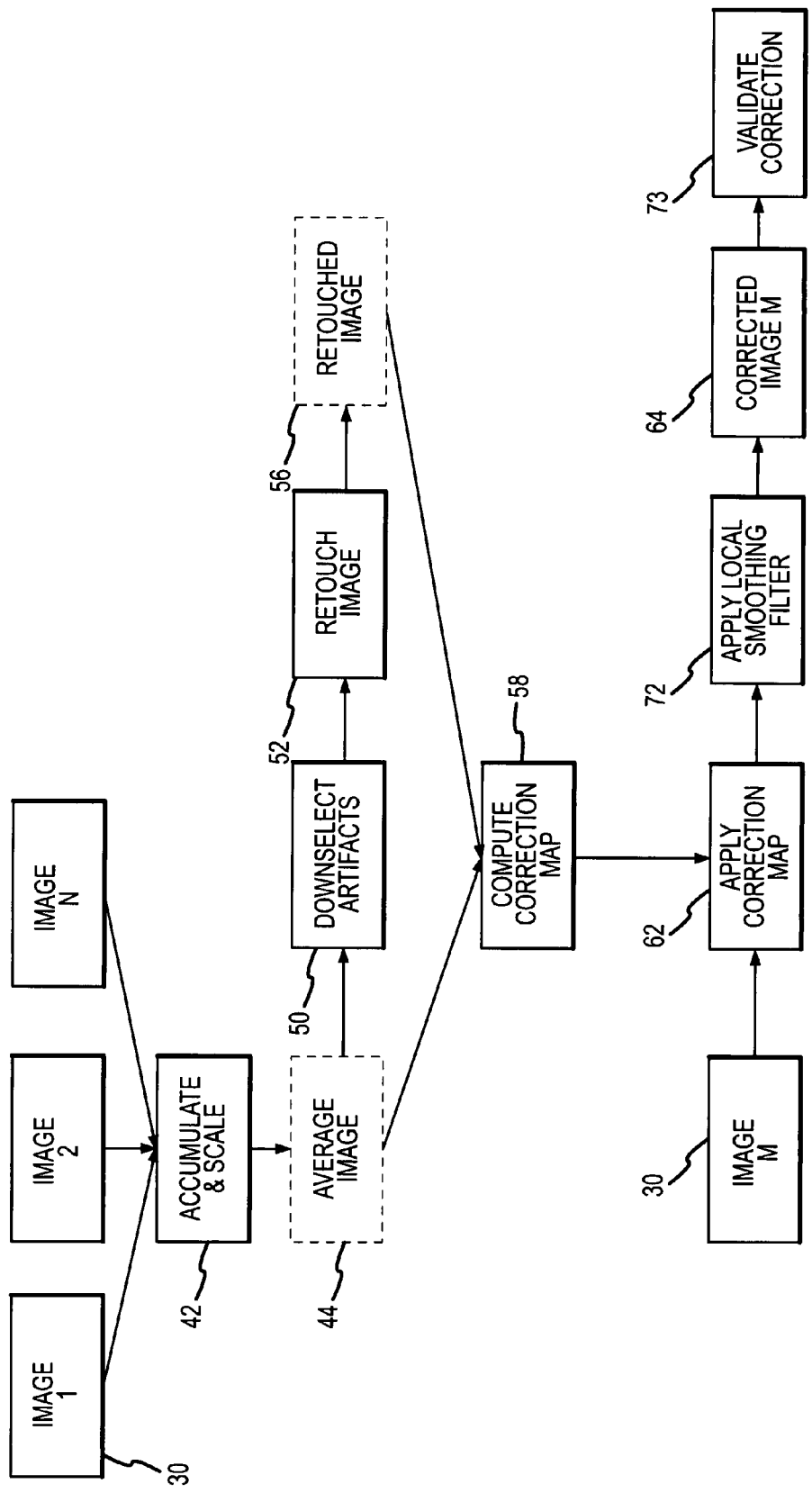
Figure 3A:
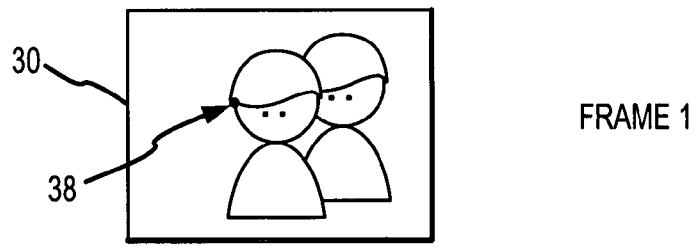
FIGS. 3a through 3c are a sequence of digital images including a semi-transparent artifact.
Figure 3B:
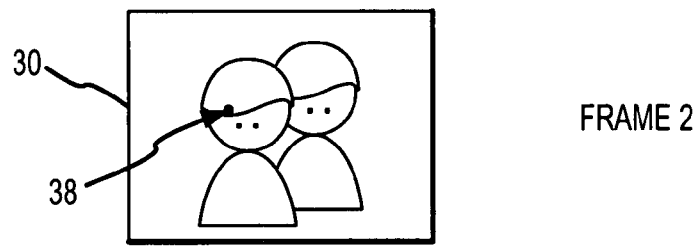
Figure 3C:
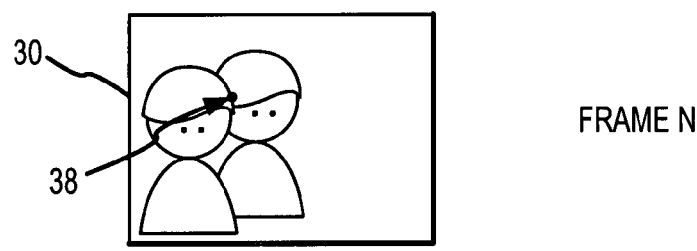
Figure 4A:
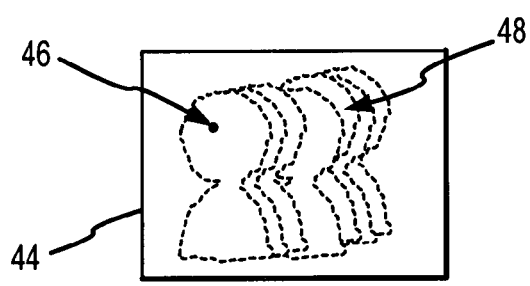
Figure 5A:
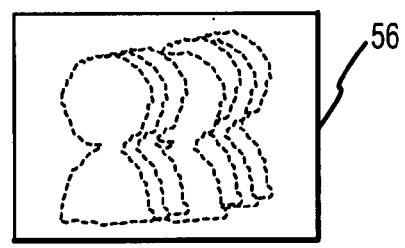

The present invention provides an efficient method and system for retouching digital images for a motion picture to remove semi-transparent artifacts or 'blotches' caused by contaminates in the optical path of the camera. This approach provides the benefit of only having to retouch a single average image that is than automatically applied via a correction power map to the entire sequence of images for the affected scene. The formation of an average image tends to reinforce the artifacts making them easier to identify and to reduce background detail making it easier to retouch the artifact.

Digital images are typically color and represented in three color planes, e.g. Red, Green and Blue; YUV; L*a*b etc. The selection of a particular color representation depends on the application and can be changed using an appropriate transformation matrix. A color file for a digital image will include three values for each pixel, e.g. the amplitude of the red, green and blue components. The present invention is applicable to any color space or grayscale imagery.

The current approach to retouching digital images is derived from a careful understanding of the artifact caused by contaminates in the optical path of the camera. First, the contaminant, hence artifact is spatially fixed with respect to the camera and digital image and temporally persistent throughout the affected scene. Second, the shadow cast by the contaminant produces a semi-transparent artifact that tends to reduce the brightness of the underlying imagery but retain the basic structure, detail and color of that content. The artifact may, although not typically, alter the color balance but does so in a consistent manner. For example, an artifact caused by dust particles absorbs more red light than green or blue. The change in brightness will vary across an image and between images on account of the non-linear response of the image brightness to the human eye, commonly called the 'gamma' of the image. The change in brightness may also vary across an artifact. For example, fringing effects near the edge of an artifact may cause the edge to be brighter than the center. However, for a given pixel (and given color plane) the affect on brightness will be approximately constant from image to image if expressed as a 'power' between the correct brightness and the masked brightness. Therefore, a map of correction powers could be applied to each contaminated image to raise the brightness to approximately the correct uncontaminated level even though the content of the image in the contaminated area of the artifact changes throughout the scene.

With an understanding of the problem and the desired solution, the problem remained as to how to generate the map of correction powers. The current approach accumulates the contaminated images to produce an average image. The formation of an average image tends to reinforce the spatially fixed, temporally persistent artifacts making them easier to identify and to reduce spatially and temporally varying background imagery making it easier to retouch the artifact to resemble the local background. The background converges to a local temporal low frequency measure of the images and the artifacts converge to a local temporal low frequency measure of the images as affected by the artifact. Therefore, a correction power for each artifact pixel computed as a non-linear coefficient between the average image and the retouched image provides a measure of the 'opacity' of the contaminant. The correction power for each non-artifact pixel is unity.

As illustrated in FIGS. 2-7, a plurality of contaminated digital images 30 for a motion picture captured either directly from a CCD digital camera 32 or indirectly from a scanner 34 that converts film 36 to digital. As described above, semi-transparent artifacts or 'blotches' 38 can be introduced into either the film 36 or camera 32 and captured in the digital image 30. The sequence of digital images for a contaminated scene is input to a computer workstation 40 that suitably includes a storage unit 41, a processor 43, input means 45 including a keyboard and/or mouse and a display 47. The workstation will typically include a software application for configuring the processor 43 to automatically perform certain steps to remove the artifacts and one or more software tools for configuring the processor 43 to enable a user to perform certain steps in the process. In some instances, the software application may be designed so that the processor performs all of the steps automatically. The software application and/or tools may be provided as computer program logic recorded on a computer useable medium 49 and download to the storage unit and processor.

According to an embodiment of the invention, the workstation processor accumulates and scales the images (step 42) to produce an average image 44 (for each color plane) that isolates spatially fixed, temporally persistent features 46 in a background 48 that converges to a local temporal low frequency measure of the images. Accumulation is essentially a temporal low-pass filtering operation that tends to reinforce or isolate features such as the blotches that are fixed relative to the camera and persistent throughout the scene. Although not illustrated in this example, desired imagery such as the children's eyes or a tree may appear as false artifacts if that portion of the scene is not moving with respect to the camera throughout the scene. Accumulation also causes the background to converge to a local temporal low frequency measure of the images e.g. a color or color gradient or low frequency structure.

Figure 7A:
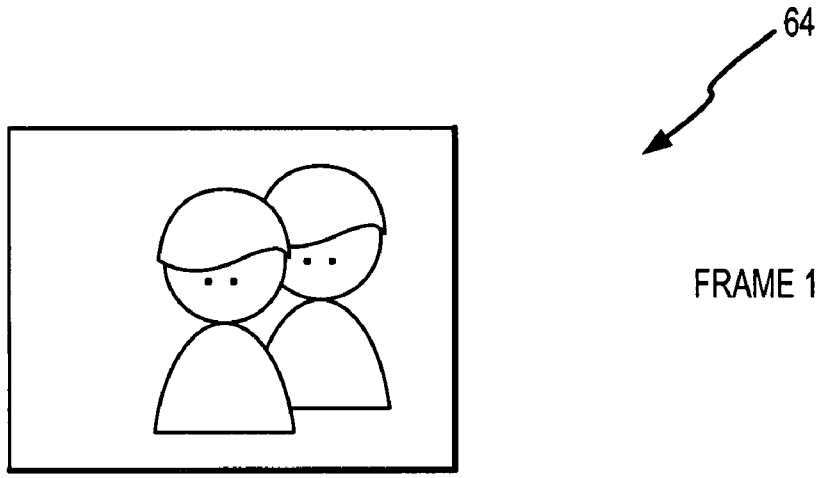
FIGS. 7a-7c are pictorial diagrams of the retouched sequence of digital images.
Figure 7B:
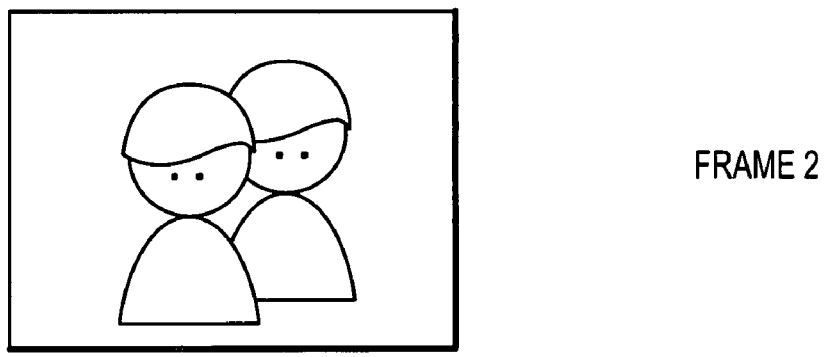
Figure 7C:
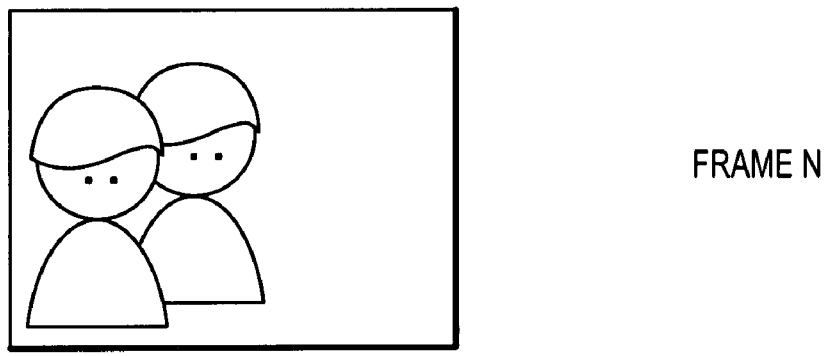

The semi-transparent artifacts, also 46 in this example, are downselected (step 50) from the isolated features to exclude false artifacts and retouched so that retouched areas 51 resemble the background 48 around the artifact 46 (step 52). Downselection and retouching can be done manually using the computer and a paint tool or with an algorithm as part of the automated software application. The processor computes a correction power 54 for each pixel in each artifact (in each color component) as a non-linear coefficient between the average image 44 and the retouched image 56 and suitably stores the powers in a correction map (step 58). The correction power for a given pixel may be determined from only amplitude information in the average and retouched images for that given pixel (in each color plane) or it may be a statistical measure from amplitude information for multiple pixels in the artifact. The processor corrects each contaminated image 30 by raising each artifact pixel (in each color plane) to its correction power (step 62) to produce a retouched image 64. The 'power' adapts the correction based on the intensity of the image in the artifact, which helps to blend with the non-linearity of the image. For simplicity, the processor determines and stores a map 66 of correction powers that has a 1-to-1 correspondence with the pixilation of the digital images and then applies the map to the entire contaminated image in which artifact pixels 68 are assigned the correction power 54 and non-artifact pixels 70 are assigned a value of one. The processor may apply a smoothing filter to the retouched areas (step 72). Furthermore, an automated or manual validation of each retouched image may be performed (step 73). The retouched images 64 sans the semi-transparent artifacts as shown in FIGS. 7a-7c are suitably stored back on storage unit 41 (or a different storage unit) and suitably written out by an appropriate mechanism such as a DVD burner or film writer as digital image files 74 on a digital storage medium, as digital data onto a medium such as a DVD or disk drive 76 or written back to analog film 78.

As described above, several of the steps may be done either manually (with computer assist via a software tool) or automatically by the processor via a software application. The primary savings in manual labor is attributable to only having to retouch a single and simpler image and having the processor automatically apply the correction map to each of the contaminated images. In the current implementation, downselection, retouching and validation are performed by a person using the appropriate computer software tools. The semi-transparent artifacts are readily apparent to any person watching a movie much less a trained technician. The technician can readily downselect the real artifacts from the features present in the average image. With the software 'painting' tools that are available, the technician can retouch each artifact to resemble or match the local background in the average image. The local background may be a uniform color, a brightness gradient of a color, a gradient change in color, low frequency structure or some combination thereof. The technician need only view the sequence of images at normal speed, e.g. 1/24 second per image, to validate the correction as opposed to manually retouching each image individually.

However, it may be possible to further reduce manual labor if not fully automate the process by partially or fully automating one or more of these steps as illustrated in FIGS. 8a-8c. The software application could be designed to configure the processor to assess the isolated features in the average image and determine which are real and which are false artifacts. For example, using the generally valid assumption that the artifact only reduces brightness of the underlying content and that the artifact in the average image should resemble the local background, the processor could identify the isolated features in the average image (step 100), compare the imagery within the isolated feature to the local background imagery (step 102) and determine whether the feature is or is not consistent with the assumptions (step 104), hence an artifact (step 106). The viability of automating the downselection process would be determined by both the accuracy of the result, e.g. are the identified artifacts over or under inclusive, and the computation expense of the algorithm. A partially automated approach would use the processor to make a first pass at downselection and than use the technician to correct and errors. The processor could be configured to assess the downselected artifacts and local background imagery and retouch the artifact. The processor can look at each color plane or a combined image to determine the appropriate values for the artifact that blend that region with the local background (step 110) and assign those values to the artifact (step 112) to produce a retouched image (step 114). In general, retouching an image is a bit 'art' and better suited to a technician than a computer algorithm but retouching the average image should be easier. The processor should be able to handle uniform backgrounds or gradients in brightness fairly easily. Variations in color or structure may be more difficult. Retouching can certainly be automated but the viability again depends on the complexity of the algorithm and the quality of the result, and the requirements on each for a given system. Lastly, the processor can be configured to validate the corrected images or sequence of images before they are released. The processor could compare the corrected artifact within a given image to the local background and determine whether the imagery is consistent with the expectations (step 120) to either reject (step 122) or validate. The processor could also compare the corrected artifact from image-to-image and determine whether the imagery is consistent with expectations (step 124) to either reject (step 126) or validate (step 128). Expectations may, for example, be that the image is relatively smooth between the local background and the artifact within any given image and that the image is relatively smooth between and two adjacent images. Different or more sophisticated techniques may be used to automate the downselection, retouching and/or validation steps.

The correction map 66 may be computed in step 58 in a number of different ways based on different assumptions, the number of contaminated images, the acceptable processing load and the required performance. In an implementation, the average and retouched images each have R, G, B values for each pixel. For each color of each pixel, the correction power is computed as the ratio of the log of the retouched value to the log of the average value. As a result, the correction map has three powers for each pixel in the image. The powers for all of the non-artifact pixels are unity because the retouched and average values are the same. When the correction map is applied to each contaminated frame, the non-artifact pixels remain unchanged and each color component of each artifact pixel is raised to its corresponding power. The correction map is used for simplicity of application. Alternately, the correction powers for a given artifact could be stored with the artifact coordinates inside the image.

Based on the typical properties of the semi-transparent artifacts certain simplifying assumptions could be made. For example, as mentioned above the artifacts typically reduce brightness without affecting the color balance. Accordingly, one could assume that the correction powers for a given pixel are all the same in an RGB color space representation and only compute and store a single correction power for each pixel. In a color representation in which luminance is a distinct component, one could compute a correction power only for the luminance component. Furthermore, one could assume that the power(s) is constant for all pixels in a given artifact or that the change in power from the center to the edges follows a particular model.

In the example given above, the correction power for a given artifact pixel was based solely on the average and retouched imagery for that pixel. Alternately, one could compute the correction power as an unweighted or weighted average of the correction powers in a neighborhood around each artifact pixel, which would tend to smooth the correction powers within a given artifact. The neighbor could be limited to only artifact pixels or could include non-artifact pixels. This might be desirable, for example, if the number of contaminated images that contribute to the average is relatively small so that the statistics for an individual pixel are less reliable.

Figure 9A:
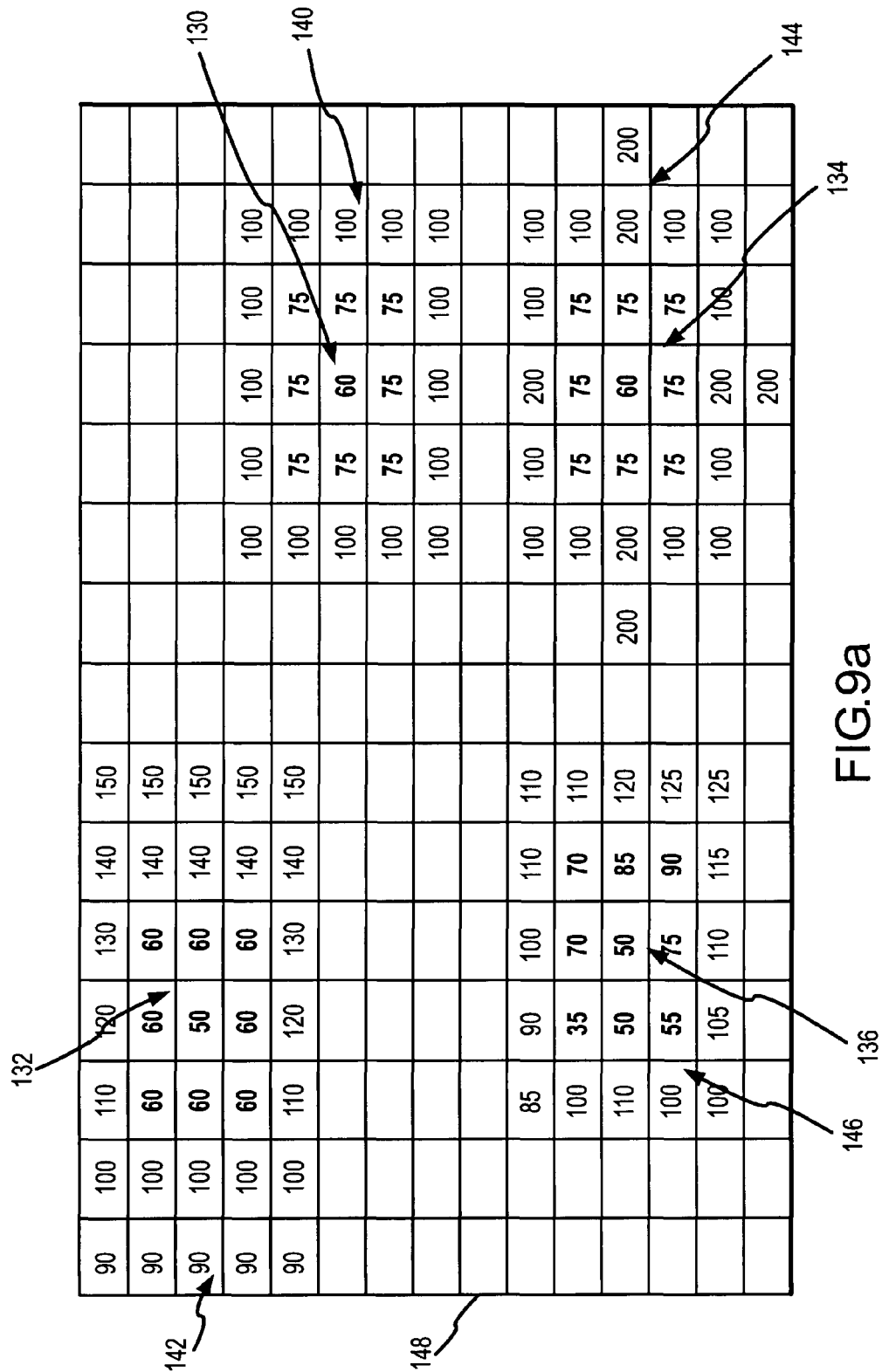
FIGS. 9a-9c are numeric diagrams of a color plane for an average image, retouched image and correction map for a number of different artifacts.
Figure 9B:
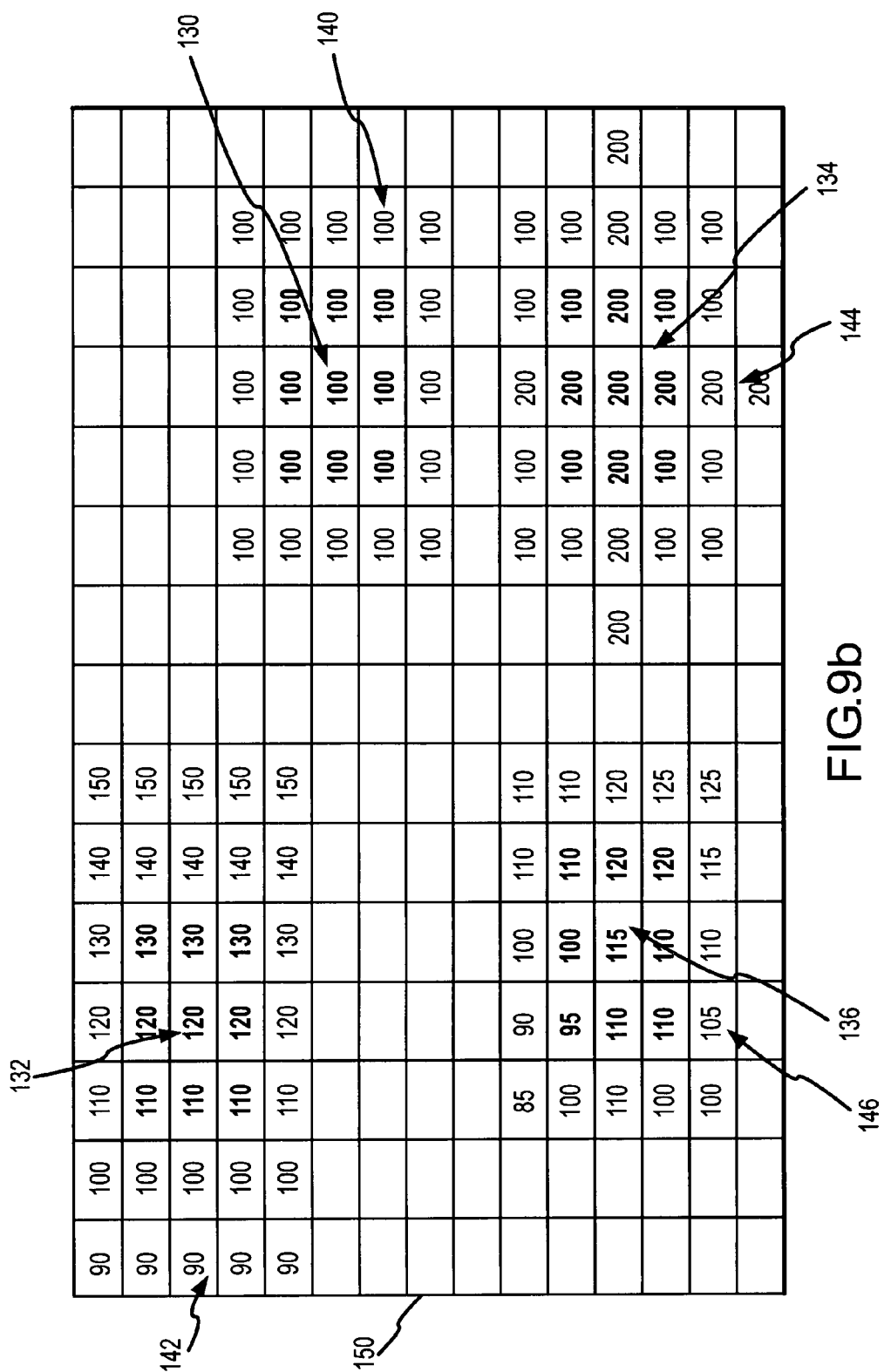
Figure 9C:
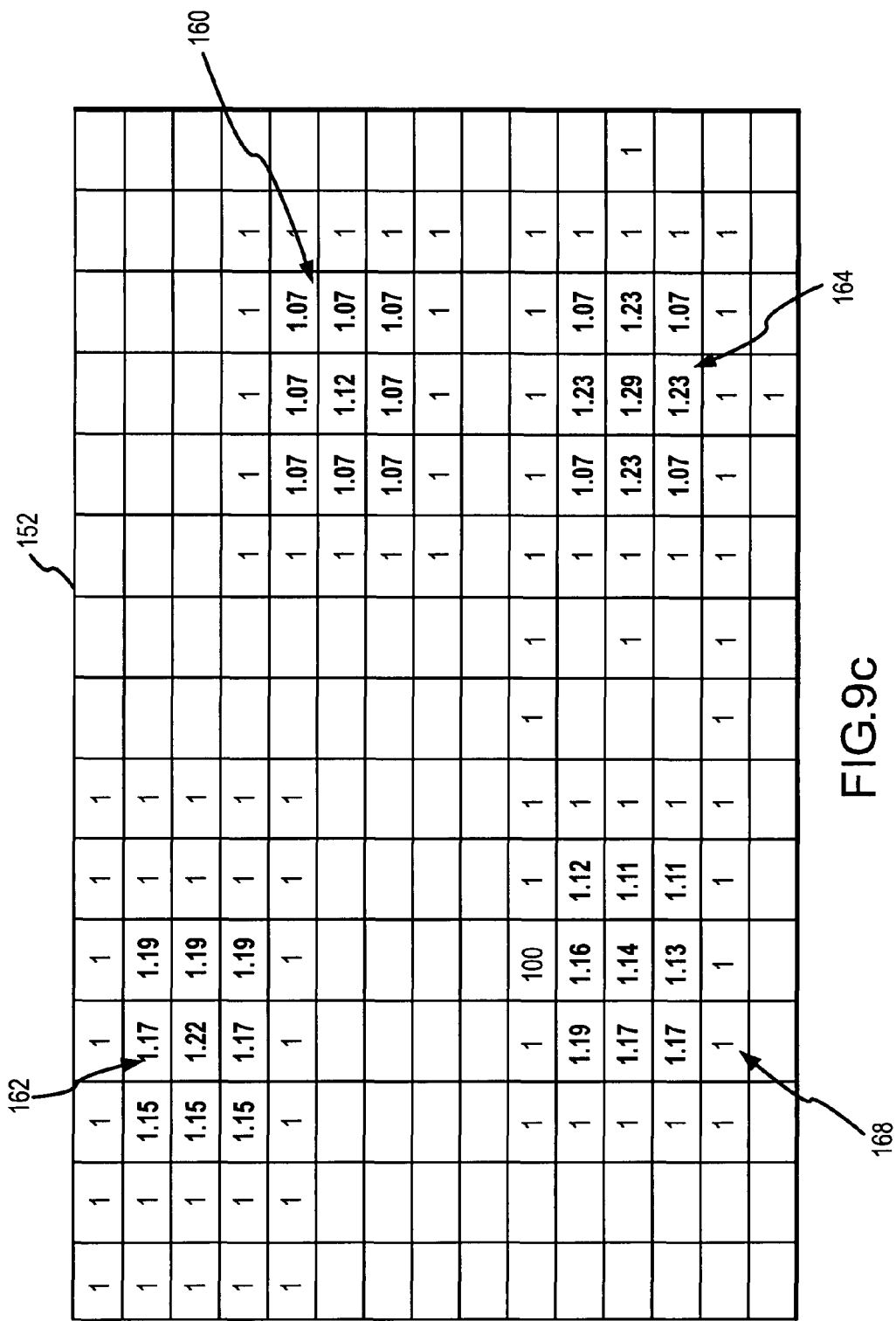

In the example illustrated in FIGS. 2-7, the artifact, local background and resultant correction power map were very simple. The artifact produces a uniformly lower brightness in a uniform background, which in turn produced uniform corrections powers throughout the artifact. FIG. 9a illustrates a single color plane for four different artifacts 130, 132, 134 and 136 in varying local backgrounds 140, 142, 144 and 146, respectively, that represent a uniform brightness, a gradient brightness, low frequency structure and a more random background in an average image 148. Artifacts 130, 132 and 134 have a reduced brightness with rest to the local background and the edges of the artifacts are brighter than the center. The artifacts are retouched to resemble or 'match' as closely as possible their respective local backgrounds to form a retouched image 150 as shown in FIG. 9b. As shown in FIG. 9c, a correction map 152 includes correction powers 160, 162, 164 and 166 for the respective artifacts. Correction powers 160, 162 and 164 were computed as the ratio of the log of the retouched value to the log of the average value for each pixel. As illustrated, correction powers 160 are uniform except the center pixel is a bit higher, correction powers 162 have a gradient that follows the local background and correction powers 164 have a structure like the underlying imagery. Correction powers 168 were calculated as the average of the pixel of interest and its 8-nearest neighbors provided the neighbor was an artifact pixel. The resulting powers are somewhat smoother than if they were calculated as individual pixels.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:
1. A method of removing semi-transparent artifacts from digital images caused by contaminants in the optical path to the camera, comprising:
   a) accumulating a plurality of contaminated images to produce an average image that isolates spatially fixed, temporally persistent features in a background that converges to a local temporal low frequency measure of the images;

b) downselecting semi-transparent artifacts from said isolated features;
c) retouching the semi-transparent artifacts to resemble the background around the artifact to produce a retouched image;
d) computing at least one correction power for each artifact pixel as a non-linear coefficient between the average image and the retouched image; and
e) correcting each contaminated image by raising each artifact pixel to its correction power to produce a corrected image,
wherein the steps of accumulating, computing and correcting are automatically performed by a computer.

2. The method of claim 1, wherein the artifacts are downselected by,
identifying the isolated features in the average image;
comparing the feature to its local background in the average image; and
if the feature is consistent with a semitransparent artifact, selecting the feature as an artifact.

3. The method of claim 2, wherein the steps of downselecting the artifacts are automatically performed by the computer.

4. The method of claim 1, wherein the artifacts are retouched by,
determining values that blend the artifact pixels to the local background around the artifact; and
assigning those values to the artifact pixels in the average image to produce the retouched image.

5. The method of claim 4, wherein the steps of retouching the artifacts are automatically performed by the computer.

6. The method of claim 1, further comprising validating the corrected images by,
determining whether the corrected artifact is consistent with the local background in the corrected image, and
determining whether the corrected artifact is consistent with the corrected artifact in adjacent images.

7. The method of claim 6, wherein the steps of validating the corrected image are automatically performed by the computer.

8. The method of claim 1, wherein the images are color images having three values per pixel.

9. The method of claim 8, wherein a correction power is computed for each of the three values per pixel.

10. The method of claim 8, wherein a single correction power is computed for all three values per pixel.

11. The method of claim 1, wherein the correction power for a pixel is a ratio of the log of the pixel value for the retouched image to the log of the pixel value for the average image.

12. The method of claim 1, wherein the correction power for a pixel is an average of the correction powers for that pixel and its neighboring pixels.

13. The method of claim 1, further comprising:
applying a spatial smoothing fitter to the corrected artifact pixels in the corrected image.

14. A semi-automated method of removing semi-transparent artifacts from digital images caused by contaminants in the optical path to the camera using a computer, comprising:
a) computer accumulation of a plurality of contaminated color images to produce an average color image that isolates spatially fixed, temporally persistent features in a background that converges to a local temporal low frequency measure of the images, each said image having three color values per pixel;
b) using a computer implemented tool to downselect semi-transparent artifacts from said isolated features;
c) using a computer implemented tool to retouch the semi-transparent artifacts to resemble the background around the artifact to produce a retouched image;
d) computer computation of a correction power for each color value of each artifact pixel as a ratio of the log of the retouched color pixel value to the log of the average color pixel value; and
e) computer correction of each contaminated image by raising each color value of artifact pixel to its correction power to produce a corrected color image.

15. An apparatus for removing semi-transparent artifacts from digital images caused by contaminants in the optical path to the camera, comprising:
a) computer means for accumulating a plurality of contaminated images to produce an average image that isolates spatially fixed, temporally persistent features in a background that converges to a local temporal low frequency measure of the images;
b) means for downselecting semi-transparent artifacts from said isolated features;
c) means for retouching the semi-transparent artifacts to resemble the background around the artifact to produce a retouched image;
d) computer means for computing at least one correction power for each artifact pixel as a non-linear coefficient between the average image and the retouched image; and
e) computer means correcting each contaminated image by raising each artifact pixel to its correction power to produce a corrected image.

16. The apparatus of claim 15, wherein the means for downselecting enables,
identification of the isolated features in the average image;
comparison of the feature to its local background in the average image; and
if the feature is consistent with a semitransparent artifact, selection of the feature as an artifact.

17. The apparatus of claim 16, where the means for downselection comprises either a computer implemented tool that enables a user to identify, compare and select or the computer that automatically identifies, compares and selects the artifacts.

18. The apparatus of claim 15, wherein the means for retouching enables,
determination of values that blend the artifact pixels to the local background around the artifact; and
assignment of those values to the artifact pixels in the average image to produce the retouched image.

19. The apparatus of claim 18, where the means for retouching comprises either a computer implemented tool that enables a user to determine and assign or the computer that automatically determines and assigns values to produce the retouched image.

20. The apparatus of claim 15, further comprising means for validating the corrected images that enables,
determination of whether the corrected artifact is consistent with the local back ground in the corrected image, and
determination of whether the corrected artifact is consistent with the corrected artifact in adjacent images.

21. The apparatus of claim 15, wherein the computer means computes the correction power for a pixel as a ratio of the log of the pixel value for the retouched image to the log of the pixel value for the average image.

22. An apparatus for removing semi-transparent artifacts from digital images caused by contaminants in the optical path to the camera, comprising:

a storage unit for storing a plurality of contaminated images, and a processor configured to accumulate a plurality of contaminated images to produce an average image that isolates spatially fixed, temporally persistent features in a background that converges to a local temporal low frequency measure of the images, enable downselection of semi-transparent artifacts from said isolated features, enable retouching of the semi-transparent artifacts to resemble the background around the artifact to produce a retouched image, compute at least one correction power for each artifact pixel as a non-linear coefficient between the average image and the retouched image, and correct each contaminated image by raising each artifact pixel to its correction power to produce a corrected image.

23. The apparatus of claim 22, wherein the processor is configured with, a software application that automatically performs the accumulation, computation and correction, and a software tool that enables a user to perform downselection and retouching.

24. A computer program product comprising a non-transitory computer useable medium having computer program logic recorded thereon for enabling a process to remove semi-transparent artifacts from digital images caused by contaminants in the optical path to the camera, the computer program comprising:

an accumulating procedure that configures the processor to accumulate a plurality of contaminated images to produce an average image that isolates spatially fixed, temporally persistent features in a background that converges to a local temporal low frequency measure of the images, a downselection procedure that configures the processor to enable downselection of semi-transparent artifacts from said isolated features, a retouch procedure that configures the processor to enable retouching of the semi-transparent artifacts to resemble the background around the artifact to produce a retouched image, a computation procedure that configures the processor to compute at least one correction power for each artifact pixel as a non-linear coefficient between the average image and the retouched image, and a correction procedure that configures the processor to correct each contaminated image by raising each artifact pixel to its correction power to produce a corrected image.

25. The computer program of claim 24, wherein said downselection procedure either configures the processor to prompt a user to downselect said semi transparent artifacts or configures the processor to automatically downselect said semi-transparent artifacts.

26. The computer program of claim 24, wherein the retouch procedure either configures the processor to prompt a user to retouch the semi-transparent artifacts or configures the processor automatically retouch the semi-transparent artifacts.

* * * * *